US008558205B2

(12) United States Patent
Ikari et al.

(10) Patent No.: US 8,558,205 B2
(45) Date of Patent: Oct. 15, 2013

(54) LIGHT DETECTION DEVICE AND SHEET PROCESSING APPARATUS INCLUDING THE SAME

(71) Applicants: Seiji Ikari, Kanagawa-ken (JP); Junji Miura, Kanagawa-ken (JP)

(72) Inventors: Seiji Ikari, Kanagawa-ken (JP); Junji Miura, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/711,949

(22) Filed: Dec. 12, 2012

(65) Prior Publication Data
US 2013/0142414 A1    Jun. 6, 2013

Related U.S. Application Data

(63) Continuation of application No. 12/713,681, filed on Feb. 26, 2010, now abandoned.

(30) Foreign Application Priority Data

Aug. 27, 2009   (JP) .................................. 2009-197190

(51) Int. Cl.
  *G06K 5/00* (2006.01)
  *G06K 9/00* (2006.01)
  *C12Q 1/68* (2006.01)
(52) U.S. Cl.
  USPC ........... 250/556; 250/200; 382/100; 382/135; 382/137; 382/140
(58) Field of Classification Search
  None
  See application file for complete search history.

(56) References Cited

U.S. PATENT DOCUMENTS

| 5,099,341 | A | * | 3/1992 | Nosaki et al. ................. 358/461 |
| 5,280,333 | A |   | 1/1994 | Wunderer |
| 5,402,249 | A | * | 3/1995 | Koseki et al. ................. 358/446 |
| 5,430,664 | A | * | 7/1995 | Cargill et al. ................. 194/207 |
| 5,915,518 | A | * | 6/1999 | Hopwood et al. ............ 194/207 |
| 6,024,202 | A | * | 2/2000 | Potter .......................... 194/207 |
| 6,064,476 | A | * | 5/2000 | Goltsos ........................ 356/213 |
| 6,297,509 | B1 |  | 10/2001 | Lipkowitsch et al. |
| 6,603,871 | B2 | * | 8/2003 | Liang ........................... 382/135 |
| 6,741,727 | B1 | * | 5/2004 | Hirasawa ..................... 382/112 |
| 6,851,609 | B2 | * | 2/2005 | Ando et al. ................... 235/454 |

(Continued)

FOREIGN PATENT DOCUMENTS

| GB | 2 240 947 | 8/1991 |
| JP | 06-308032 | 11/1994 |

(Continued)

*Primary Examiner* — Jason M Repko
*Assistant Examiner* — Avinash J Yentrapati
(74) *Attorney, Agent, or Firm* — Pillsbury Winthrop Shaw Pittman, LLP (57) ABSTRACT

Presented is a light detection device including a first detecting portion detecting fluorescence from a first detection position on a conveyor path, a second detecting portion detecting afterglow from a second detection position on the conveyor path, a lighting portion applying excitation light over a range including the first detection position but not the second detection position, a first reference member including fluorescent material emitting fluorescence and emitting reference light toward the first detecting portion, a second reference member emitting reference light toward the second detecting portion, the reference light not influencing a result of detection by the second detecting portion, and a correction controller correcting a detection result by the first detecting portion based on the reference light detected by the first detecting portion and correcting a detection result by the second detecting portion based on the reference light detected by the second detecting portion.

12 Claims, 8 Drawing Sheets

(56) References Cited

U.S. PATENT DOCUMENTS

| | | | |
|---|---|---|---|
| 6,918,482 B2* | 7/2005 | Thierauf | 194/207 |
| 6,975,435 B1* | 12/2005 | Maitani et al. | 358/475 |
| 7,046,346 B2* | 5/2006 | Premjeyanth et al. | 356/71 |
| 7,064,874 B2* | 6/2006 | Imai | 358/498 |
| 7,110,093 B2* | 9/2006 | Kamijo | 356/71 |
| 7,184,133 B2* | 2/2007 | Coombs et al. | 356/71 |
| 2002/0015145 A1* | 2/2002 | Numata | 356/71 |
| 2003/0063327 A1* | 4/2003 | Sone | 358/461 |
| 2004/0095619 A1* | 5/2004 | Akaba | 358/509 |
| 2004/0233479 A1* | 11/2004 | Hashizume | 358/461 |
| 2005/0243384 A1* | 11/2005 | Sone | 358/474 |
| 2006/0209367 A1* | 9/2006 | Misaka | 358/500 |
| 2007/0189595 A1* | 8/2007 | Giering | 382/137 |
| 2009/0028415 A1* | 1/2009 | Giering et al. | 382/137 |
| 2012/0226600 A1* | 9/2012 | Dolev | 705/38 |

FOREIGN PATENT DOCUMENTS

| | | |
|---|---|---|
| JP | 3790931 | 4/2006 |
| JP | 2008-192534 | 7/2008 |
| WO | WO 95/19019 | 7/1995 |

* cited by examiner

LIGHT DETECTION DEVICE AND SHEET PROCESSING APPARATUS INCLUDING THE SAME

CROSS-REFERENCE TO RELATED APPLICATION

This is a Continuation Application of co-pending U.S. application Ser. No. 12/713,681, filed Feb. 26, 2010, and for which priority is claimed under 35 U.S.C. §120. This application is based upon and claims the benefit of priority from Japanese Patent Application No. 2009-197190, filed on Aug. 27, 2009, the entire contents of all applications are incorporated herein by reference in their entireties.

TECHNICAL FIELD

The present invention relates to a light detection device for detecting light from a sheet being conveyed, and a sheet processing apparatus including the same.

BACKGROUND

Heretofore, sheet processing apparatuses for counting and distinguishing various sheets such as banknotes have been brought to practical use. A sheet processing apparatus takes in sheets inserted in an insert portion one by one and conveys the sheets to a light detection device. The light detection device detects light from each of the sheets and acquires an image based on the detected light. The sheet processing apparatus determines the type and authenticity of the sheet based on the acquired image. The sheet processing apparatus also determines whether or not the sheet can be recirculated, based on the acquired image. The sheet processing apparatus stacks the sheets in a state in which the sheets are classified by type based on results of the determinations.

On sheets to be processed by the sheet processing apparatus, there are printed fluorescent printed information (first printed information) and phosphorescent printed information (second printed information). The fluorescent printed information is information printed in ink (fluorescent ink) containing fluorescent material. The fluorescent material is excited by excitation light (e.g., ultraviolet rays) or the like emitted from an excitation light source. The excited fluorescent material emits light (fluorescence). When the irradiation with the excitation light is interrupted, the fluorescent material stops emitting fluorescence.

The phosphorescent printed information is information printed in ink (phosphorescent ink) containing phosphorescent material. The phosphorescent material is excited by excitation light (e.g., ultraviolet rays) or the like emitted from an excitation light source. The excited phosphorescent material emits light. When the irradiation with the excitation light is interrupted, the phosphorescent material emits light (afterglow) which gradually attenuates with time.

Japanese Patent No. 3790931, for example, discloses a light detection device including an excitation light source, a sensor for detecting fluorescence, and a sensor for detecting phosphorescence.

In general, a light detection device for detecting fluorescence and phosphorescence includes a fluorescence detecting portion on the upstream side of a conveyor path along which sheets are conveyed. Further, the light detection device includes a phosphorescence detecting portion downstream of the fluorescence detecting portion.

The fluorescence detecting portion irradiates a sheet with excitation light from an excitation light source to excite the fluorescent and phosphorescent materials. The fluorescence detecting portion detects fluorescence emitted from the excited fluorescent material and reads fluorescent printed information.

The phosphorescence detecting portion detects afterglow emitted from the phosphorescent material after interruption of the irradiation with the excitation light by the fluorescence detecting portion, and reads phosphorescent printed information.

The amount of light emitted by the excitation light source changes due to aging. Also, the sensitivities of the sensors of the detecting portions may change. For these reasons, light detection devices have generally been brought to practical use, each of which includes a fluorescent reference plate in the vicinity of a detection position of a detecting portion.

In this case, the fluorescence detecting portion includes a fluorescent glass as a fluorescent reference plate. The fluorescent glass emits fluorescence as a detection reference toward a sensor. The sensor and the fluorescent glass are disposed to face each other across a conveyor path of a sheet processing apparatus. The fluorescence detecting portion detects fluorescence emitted from the fluorescent glass while no sheets are being conveyed. The fluorescence detecting portion corrects the amount of light emitted by a light emitting element or the sensitivity of the sensor based on the value of the detected fluorescence.

However, light from an excitation light source does not reach a detection position of a phosphorescence detecting portion. Accordingly, if a fluorescent glass is disposed at the detection position of the phosphorescence detecting portion, the fluorescent glass is not excited. Thus, there has been the problem that correction cannot be performed on a sensor of the phosphorescence detecting portion.

SUMMARY

An object of the present invention is to provide a light detection device in which correction can be performed on a fluorescence detecting portion and a phosphorescence detecting portion, and a sheet processing apparatus including this light detection device.

An aspect of the present disclosure relates to a light detection device containing a first detecting portion to detect fluorescence from a first detection position on a conveyor path along which a sheet is conveyed; a second detecting portion to detect afterglow from a second detection position on the conveyor path along which the sheet is conveyed; a lighting portion to apply excitation light over a range including the first detection position and not including the second detection position; a first reference member to emit reference light toward the first detecting portion, the first reference member including fluorescent material which emits fluorescence by being excited by the lighting portion; a second reference member to emit reference light toward the second detecting portion when the sheet is present at the second detection position, the reference light not influencing a result of detection by the second detecting portion; and a correction controller to correct a result of detection by the first detecting portion based on the reference light detected by the first detecting portion and to correct a result of detection by the second detecting portion based on the reference light detected by the second detecting portion.

Another aspect of the present disclosure relates to a sheet processing apparatus containing: a conveyor path to convey a sheet; a first detecting portion to detect fluorescence from a first detection position on the conveyor path along which the sheet is conveyed; a second detecting portion to detect afterglow from a second detection position on the conveyor path along which the sheet is conveyed; a lighting portion to apply excitation light over a range including the first detection position and not including the second detection position; a first reference member to emit reference light toward the first detecting portion, the first reference member including fluorescent material which emits fluorescence by being excited by the lighting portion; a second reference member to emit reference light toward the second detecting portion when the sheet is present at the second detection position, the reference light not influencing a result of detection by the second detecting portion; a correction controller to correct a result of detection by the first detecting portion based on the reference light detected by the first detecting portion and to correct a result of detection by the second detecting portion based on the reference light detected by the second detecting portion; a determination portion to determine whether or not the sheet contains each of fluorescent printed information and phosphorescent printed information, based on a fluorescent image detected by the first detecting portion and an afterglow image detected by the second detecting portion; and a classification processor to determine a type of the sheet based on a result of the determination by the determination portion and to classify the sheet by type.

DETAILED DESCRIPTION

Hereinafter, a light detection device according to a first embodiment of the present invention and a sheet processing apparatus including this light detection device will be described in detail with reference to the drawings.

Figure 1:
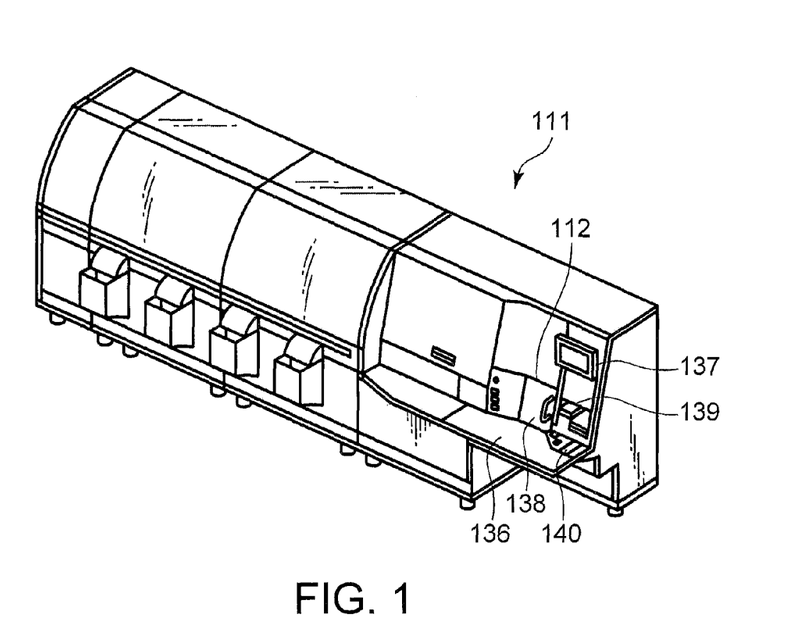
FIG. 1 is a perspective view showing an example of the configuration of a sheet processing apparatus according to one embodiment.
Figure 2:
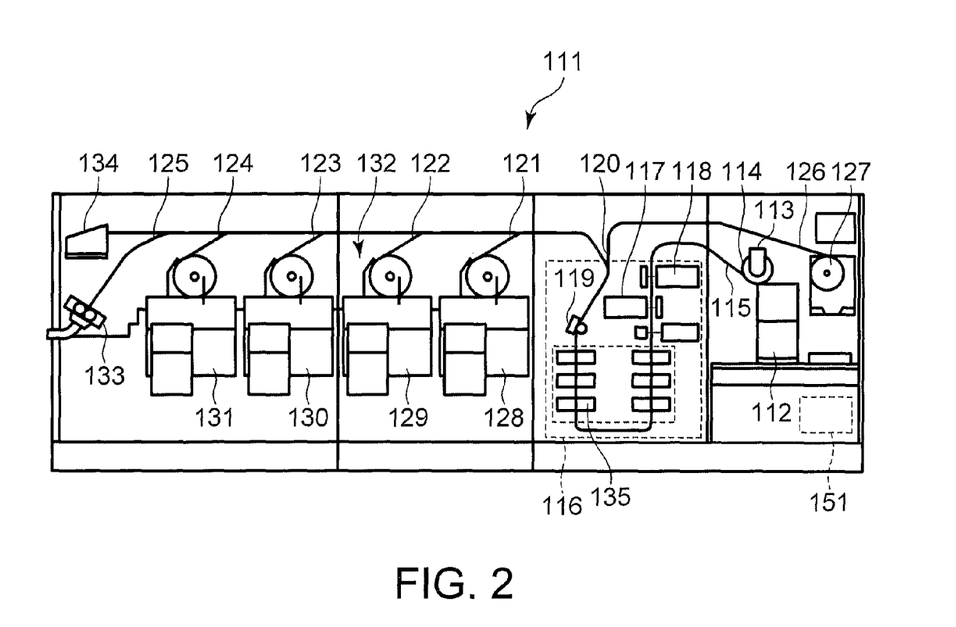
FIG. 2 is a schematic front view showing an example of the configuration of the sheet processing apparatus shown in FIG. 1.

FIGS. 1 and 2 are views for, explaining an example of the configuration of a sheet processing apparatus 111 according to the first embodiment of the present invention. The sheet processing apparatus 111 inspects sheets, and bands sheets qualified for recirculation.

As shown in FIG. 1, the sheet processing apparatus 111 has, on the outside thereof, an insert portion 112, an operating portion 136, an operation/display panel 137, a door 138, a take-out port 139, and a keyboard 140.

The insert portion 112 is intended for the insertion of sheets. The insert portion 112 receives a pile of sheets collectively. The operating portion 136 receives various operation inputs from an operator. The operation/display panel 137 displays various operation guides, processing results, and the like to the operator. Here, the operation/display panel 137 may be configured as a touch screen. In this case, the sheet processing apparatus 111 detects various operation inputs based on buttons displayed on the operation/display panel 137 and operations performed on the operation/display panel 137 by the operator.

The door 138 is used for opening and closing an insert cavity of the insert portion 112. The take-out port 139 is intended for taking out sheets from a stacker stacked with sheets disqualified for the recirculation by the sheet processing apparatus 111. The keyboard 140 receives various operation inputs from the operator.

As shown in FIG. 2, the sheet processing apparatus 111 has therein, the insert portion 112, a take-out portion 113, an absorption roller 114, a conveyor path 115, an inspection portion 116, gates 120 to 125, a rejection sheet conveyor path 126, a rejection sheet stacker 127, stack/band portions 128 to 131 a cutting portion 133, and a stacker 134. The sheet processing apparatus 111 further includes a main controller 151 for comprehensively controlling the operation of each portion of the sheet processing apparatus 111.

The take-out portion 113 is provided above the insert portion 112. The take-out portion 113 has the absorption roller 114. The absorption roller 114 is provided to be in contact with the top, in the stacking direction, of a stack of sheets set in the insert portion 112. Specifically, when the absorption roller 114 rotates, the sheets set in the insert portion 112 are taken into the apparatus one by one from the top of the stack in the stacking direction. The absorption roller 114 has the function of, for example, taking out one sheet per revolution. Thus, the absorption roller 114 takes out sheets at a constant pitch. Each of the sheets taken in by the absorption roller 114 is guided to the conveyor path 115.

The conveyor path 115 is a conveyor portion for conveying the sheets to each portion of the sheet processing apparatus 111. The conveyor path 115 includes a conveyor belt, a drive pulley, and the like, which are not shown. In the conveyor path 115, the conveyor belt is operated by an unillustrated drive motor. In the conveyor path 115, the sheets taken in by the absorption roller 114 are conveyed by the conveyor belt at a constant speed. It should be noted that in the following description, the side of the conveyor path 115 closer to the take-out portion 113 is referred to as an upstream side, and the side of the conveyor path 115 closer to the stacker 134 is referred to as a downstream side.

The inspection portion 116 is provided along the conveyor path 115 extending from the take-out portion 113. The inspection portion 116 includes an image reader 117, an image reader 118, a thickness inspection portion 119, and a light detection device 135. The inspection portion 116 detects optical characteristic information and magnetic characteristic information on a sheet. Based on the information, the sheet processing apparatus 111 determines the type of the sheet. The sheet processing apparatus 111 also determines the degree of wear and soiling of the sheet. The sheet processing apparatus 111 further determines the orientation of the sheet in regard to the front and reverse sides. The sheet processing apparatus 111 still further determines whether the sheet is genuine or forged.

The image readers 117 and 118 are provided to face each other across the conveyor path 115. The image readers 117 and 118 read images on both sides of the sheet being conveyed along the conveyor path 115. Each of the image readers 117 and 118 includes a CCD camera. The sheet processing apparatus 111 acquires pattern images on the front and reverse sides of the sheet based on the images captured by the image readers 117 and 118.

The image readers 117 and 118 temporarily respectively store the read images in unillustrated memory in the inspection portion 116. In accordance with operation inputs, the images stored in this memory are displayed on the operation/display panel 137 by the sheet processing apparatus 111.

The thickness inspection portion 119 inspects the thickness of the sheet being conveyed along the conveyor path 115. For example, in the case where the detected thickness is not less than a specified value, the sheet processing apparatus 111 detects a double taking of sheets.

The light detection device 135 detects fluorescence and afterglow from the sheet being conveyed along the conveyor path 115 to acquire fluorescent printed information and phosphorescent printed information. The light detection device 135 will be described in detail later.

The inspection portion 116 includes a magnetic sensor, which are not shown, and the like. The magnetic sensor detects magnetic characteristic information on the sheet.

The gates 120 to 125 are disposed in this order downstream of the inspection portion 116 along the conveyor path 115. The gates 120 to 125 are controlled by the main controller 151. The main controller 151 controls the operation of the gates 120 to 125 based on results of inspections by the inspection portion 116. Thus, the main controller 151 performs control so that the sheet being conveyed along the conveyor path 115 may be conveyed to a predetermined processing portion.

Through the gate 120 disposed immediately behind the inspection portion 116, the rejection sheet conveyor path 126 branches off from the conveyor path 115. Specifically, the main controller 151 switches opening and closing of the gate 120 so that only illegal sheets, uninspectable notes and the like may be conveyed to the rejection sheet conveyor path 126. Here, the illegal sheets are sheets determined to be non-authorized sheets (legal sheets) based on results of inspections by the inspection portion 116, and the uninspectable notes are notes not inspectable by the inspection portion 116.

At the end of the rejection sheet conveyor path 126, the rejection sheet stacker (rejection portion) 127 is provided. The rejection sheet stacker 127 is stacked with the aforementioned rejected sheets and uninspectable notes without any turn from the state where the sheets and notes are taken out by the take-out portion 113. The sheets stacked in the rejection sheet stacker 127 can be taken out through the take-out port 139.

At ends of paths branched off by the gates 121 to 124, the stack/band portions 128 to 131 (collectively referred to as a stack/band unit 132) are provided, respectively. In the stack/band unit 132, sheets qualified for the recirculation are stacked to be classified by type and orientation in regard to front and reverse sides. The stack/band unit 132 bands and stores the stacked sheets in bundles of a predetermined number each.

At the end of a path branched off by the gate 125, the cutting portion 133 is disposed. The cutting portion 133 cuts sheets and stores the cut sheets. It should be noted that the sheets conveyed to the gate 125 are authorized sheets determined to be unfit for recirculation. At the end of the other path branched off by the gate 125, the stacker 134 is disposed. In the case where a worn-note cutting mode is selected, the main controller 151 controls the gate 125 so that sheets may be conveyed to the cutting portion 133. On the other hand, in the case where the worn-note cutting mode is not selected, the main controller 151 controls the gate 125 so that sheets may be conveyed to the stacker 134.

The main controller 151 counts sheets stacked in the stack/band unit 132 and counts sheets cut by the cutting portion 133.

Figure 3:
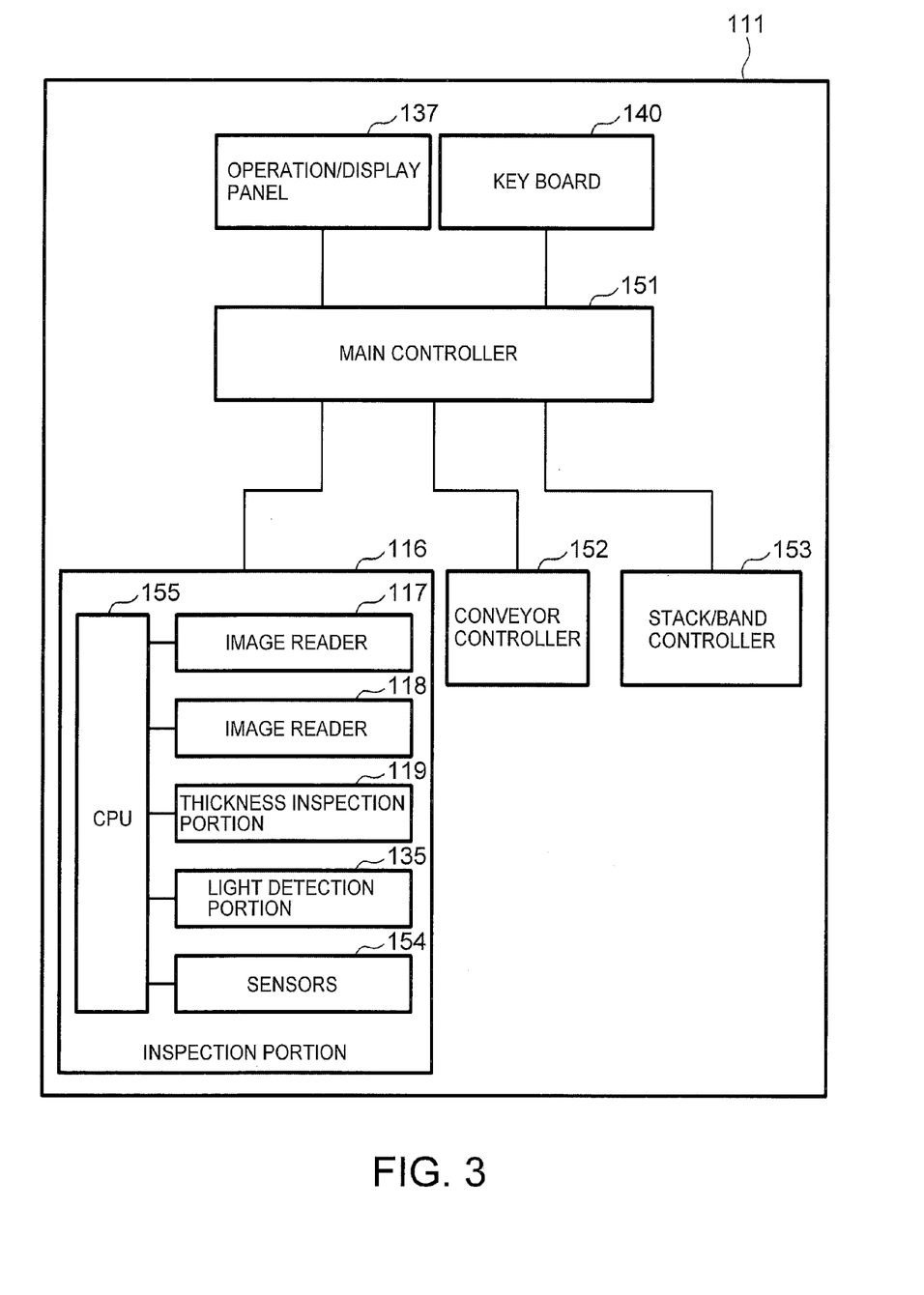
FIG. 3 is a block diagram showing the configuration of a control system of the sheet processing apparatus shown in FIGS. 1 and 2.

FIG. 3 is a block diagram for explaining an example of the configuration of a control system of the sheet processing apparatus 111 shown in FIGS. 1 and 2. As shown in FIG. 3, the inspection portion 116, a conveyor controller 152, a stack/band controller 153, the operation/display panel 137, the keyboard 140, and the like are connected to the main controller 151, which comprehensively controls the entire apparatus.

The main controller 151 is responsible for the overall control of the sheet processing apparatus 111. The main controller 151 controls the conveyor controller 152 and the stack/band controller 153 based on an operation signal inputted through the operation/display panel 137 and results of inspections by the inspection portion 116.

The inspection portion 116 includes the image readers 117 and 118, the thickness inspection portion 119, the light detection device 135, sensors 154, and a CPU 155.

The image readers 117 and 118 read images on both sides of a sheet being conveyed along the conveyor path 115. The thickness inspection portion 119 inspects the thickness of the sheet being conveyed along the conveyor path 115.

The light detection device 135 detects fluorescence and afterglow from the sheet being conveyed along the conveyor path 115 to acquire fluorescent printed information and phosphorescent printed information.

The sensors 154 are, for example, a magnetic sensor and the like. The magnetic sensor detects magnetic characteristic information from the sheet being conveyed along the conveyor path 115.

The CPU 155 determines the type, the degree of wear and soiling, the orientation in regard to the front and reverse sides, the authenticity, and the like of the sheet being conveyed along the conveyor path 115 based on results of inspections by the image readers 117 and 118, the thickness inspection portion 119, the light detection device 135, the sensors 154, and the like.

The conveyor controller 152 controls the take-out portion 113, the conveyor path 115, the rejection sheet conveyor path 126, and the gates 120 to 125 under the control of the main controller 151. Thus, the conveyor controller 152 controls the taking in and conveyance of sheets. The conveyor controller 152 also performs a classification process for classifying determined sheets by type. In other words, the conveyor controller 152 functions as a classification portion.

The stack/band controller 153 controls the rejection sheet stacker 127 and the stack/band portions 128 to 131 under the control of the main controller 151. Thus, the stack/band controller 153 controls the stacking and banding of sheets.

It is assumed that on sheets to be processed by the sheet processing apparatus 111 according to this embodiment, fluorescent printed information (first printed information) is printed in fluorescent ink containing fluorescent material and phosphorescent printed information (second printed information) is printed in phosphorescent ink containing phosphorescent material, for example.

Fluorescent and phosphorescent materials are excited by excitation light such as light, heat, ultraviolet rays, or X-rays from outside to emit light. The amounts of light emitted by fluorescent and phosphorescent materials increase with increasing excitation light irradiation time. The amounts of light emitted by fluorescent and phosphorescent materials become saturated in the case where excitation light irradiation time reaches emission saturation time. Emission saturation time is the time required to saturate the amount of light emitted by fluorescent or phosphorescent material. Emission saturation time depends on characteristics of material.

Fluorescent and phosphorescent materials transition to non-emitting states when decay time has elapsed since emission saturation. Decay time is the time it takes for fluorescent or phosphorescent material to transition from a state in which an emission amount is saturated to a non-emitting state. Decay time also depends on characteristics of the material of fluorescent or phosphorescent material.

The emission saturation time of fluorescent material is shorter than that of phosphorescent material. The decay time of fluorescent material is also shorter than that of phosphorescent material.

Accordingly, the light detection device 135 of this embodiment irradiates the fluorescent and phosphorescent materials with excitation light until the amounts of light emitted by the fluorescent and phosphorescent materials become sufficiently saturated. When time corresponding to the decay time of the fluorescent material has elapsed since the irradiation with the excitation light has been interrupted, the fluorescent material transitions to a state in which fluorescence is not emitted. By detecting light with this timing, the light detection device 135 can detect only phosphorescence (afterglow) emitted by the phosphorescent material.

Figure 4:
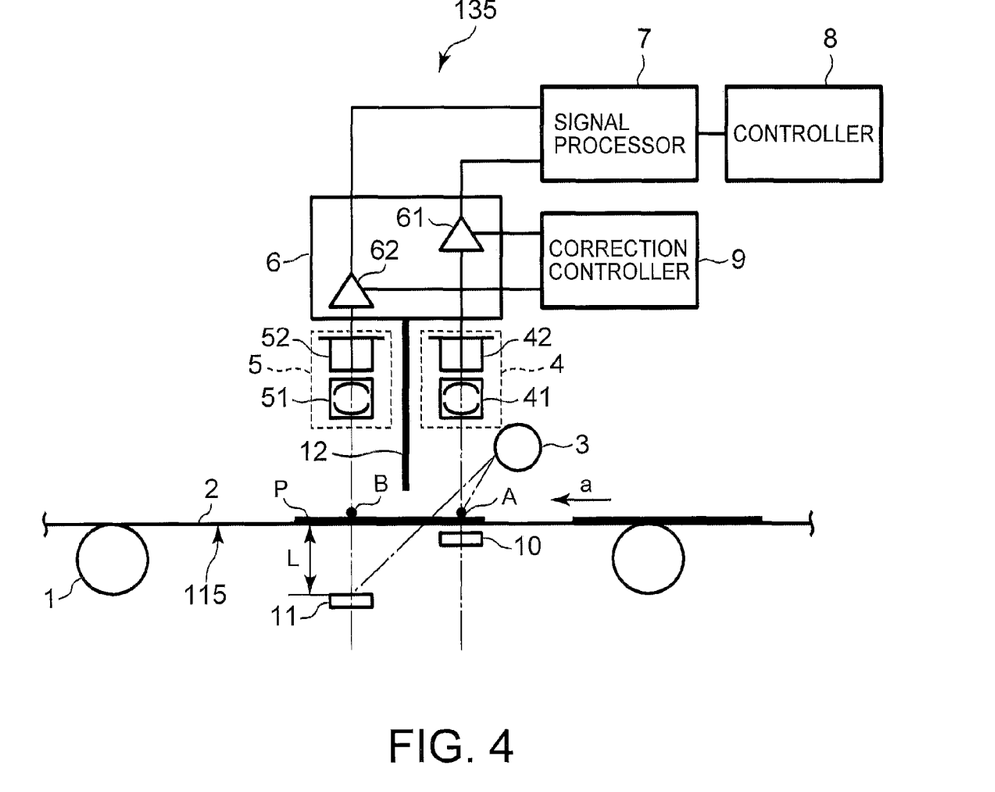
FIG. 4 is a simplified diagram schematically showing the configuration of a light detection device according to a first embodiment.

FIG. 4 is an explanatory diagram schematically showing the configuration of the light detection device 135 shown in FIGS. 2 and 3. As shown in FIG. 4, the light detection device 135 is provided in the vicinity of the conveyor path 115 which includes a drive pulley 1, a conveyor belt 2, and the like. Sheets P is conveyed along the conveyor path 115 in the direction indicated by arrow a.

The light detection device 135 includes a lighting portion 3, first and second detecting portions 4 and 5, an amp circuit 6, a signal processor 7, a controller 8, a correction controller 9, first and second fluorescent reference plates 10 and 11, and a shield plate 12.

The lighting portion 3 emits excitation light, e.g., ultraviolet rays or the like. The lighting portion 3 applies the excitation light to a sheet P being conveyed along the conveyor path 115. The lighting portion 3 emits light over a range including at least a detection position A of the first detecting portion 4.

The lighting portion 3 includes, for example, a fluorescent tube outputting ultraviolet rays or a cold-cathode tube. The lighting portion 3 can continuously emit ultraviolet rays by a high-frequency voltage being applied thereto.

In recent years, the luminance of LED lamps have been increased. Accordingly, a lighting device may be employed in which LED lamps are arranged in an array along the conveyor path 115. Alternatively, a lighting device may be employed which emits light toward a detection position using a light source, such as a mercury lamp, that emits light containing ultraviolet rays.

This embodiment is described by taking as examples fluorescent material and phosphorescent material which emit light by being irradiated with ultraviolet rays. However, the present invention is not limited to this. For example, in the case where fluorescent material and phosphorescent material which emit light by being excited by infrared rays are detected, the lighting portion 3 includes a lighting device which outputs infrared rays. In other words, the lighting portion 3 is appropriately modified in accordance with characteristics of substances to be detected.

Each of the first and second detecting portions 4 and 5 includes, for example, a CMOS or CCD line image sensor and a lens for receiving light. Specifically, the first detecting portion 4 includes a lens 41 and a sensor 42. On the other hand, the second detecting portion 5 includes a lens 51 and a sensor 52.

The lens 51 receives light from the predetermined detection position A on the conveyor path 115. The lens 41 images the received light onto the sensor 42. The sensor 42 converts the received light into an electric signal. The lens 51 receives light from a predetermined detection position B on the conveyor path 115. The lens 51 images the received light onto the sensor 52. The sensor 52 converts the received light into an electric signal.

In the case where the first and second detecting portions 4 and 5 perform color separation on the detected light, the first and second detecting portions 4 and 5 include array sensors such as color line image sensors. In the case where the first and second detecting portions 4 and 5 do not need to perform color separation, the first and second detecting portions 4 and 5 include monochrome image sensors, photodiode arrays, or the like. In the case where the first and second detecting portions 4 and 5 do not need to have widths in the scanning directions, the first and second detecting portions 4 and 5 may be formed by a single light receiving element.

The first and second detecting portions 4 and 5 may include, for example, back-thinned image sensors. The first and second detecting portions 4 and 5 may further include TDI (Time Delay Integration) image sensors or the like.

In the case where the first and second detecting portions 4 and 5 are formed by a single light receiving element, the first and second detecting portions 4 and 5 may be formed by an avalanche photodiode, a photomultiplier tube, or the like.

The first detecting portion 4 detects fluorescence from the sheet P. The second detecting portion 5 detects afterglow from the sheet P.

The amp circuit 6 amplifies signals detected by the first and second detecting portions 4 and 5. The amp circuit 6 includes an amplifier 61 for amplifying a signal detected by the first detecting portion 4 and an amplifier 62 for amplifying a signal detected by the second detecting portion 5. The gains of the amplifiers are controlled by the correction controller 9. The amp circuit 6 transmits amplified signals to the signal processor 7.

The signal processor 7 receives the signals transmitted from the amp circuit 6. The signal processor 7 performs analog-to-digital conversion (A/D conversion) of the received signals. The signal processor 7 acquires image information as results of the A/D conversion. In other words, the signal processor 7 samples the received signals to acquire image information.

The acquired image information corresponds to per-line light detected by the first and second detecting portions 4 and 5. The signal processor 7 performs the above-described processing for the entire sheet P. Thus, the signal processor 7 acquires a fluorescent image and an afterglow image of the sheet P.

The controller 8 is responsible for the overall control of the light detection device 135. The controller 8 includes a CPU, a buffer memory, a program memory, a nonvolatile memory, and the like. The CPU performs various kinds of arithmetic processing. The buffer memory temporarily stores results of arithmetic by the CPU. The program memory and the nonvolatile memory stores various programs executed by the CPU, control data, and the like. The controller 8 can perform various kinds of processing by the CPU executing programs stored in the program memory.

For example, the controller 8 controls the respective timings with which the first and second detecting portions 4 and 5 detect light. The nonvolatile memory of the controller 8 stores reference data beforehand. The controller 8 compares the image information detected from the sheet P and the reference data stored in the nonvolatile memory. The controller 8 determines, based on the result of the comparison, whether or not the image information detected from the sheet P contains fluorescent printed information and phosphorescent printed information. In other words, the controller 8 functions as a determination portion.

The correction controller 9 controls the respective gains of the amplifiers 61 and 62 of the amp circuit 6. The correction controller 9 controls the gain of the amplifier 61 in accordance with the level of reference light emitted from the first fluorescent reference plate 10. The correction controller 9 also controls the gain of the amplifier 62 in accordance with the level of reference light emitted from the second fluorescent reference plate 11.

The light intensity of afterglow is weaker than that of fluorescence. In other words, in the case where the gains of the amplifiers 61 and 62 have the same value, a signal detected by the second detecting portion 5 is weaker than a signal detected by the first detecting portion 4. For this reason, the correction controller 9 sets the gain of the amplifier 62 higher than the gain of the amplifier 61. This enables the light detection device 135 to obtain signals on comparable levels for fluorescence and afterglow.

The first fluorescent reference plate 10 supplies the first detecting portion 4 with reference light for use in correcting the gain of the amplifier 61 of the amp circuit 6. In other words, the first fluorescent reference plate 10 functions as a reference member for supplying the first detecting portion 4 with the reference light. The first fluorescent reference plate 10 is disposed at a position facing the first detecting portion 4 across the conveyor path 115. Further, the first fluorescent reference plate 10 is disposed at least on an extension of a line connecting the first detecting portion 4 and the detection position A.

The first fluorescent reference plate 10 includes, for example, glass (fluoroglass) or the like containing fluorescent material. For example, in the case where ultraviolet rays are applied to fluoroglass, the fluorescent material contained in the fluoroglass emits fluorescence. Specifically, when the excitation light is applied to the first fluorescent reference plate 10, the first fluorescent reference plate 10 emits fluorescence toward the first detecting portion 4. In other words, when there is no sheet P at the detection position A, at least part of the first fluorescent reference plate 10 appears in an image captured by the first detecting portion 4.

The second fluorescent reference plate 11 supplies the second detecting portion 5 with reference light for use in correcting the gain of the amplifier 62 of the amp circuit 6. In other words, the second fluorescent reference plate 11 functions as a reference member for supplying the second detecting portion 5 with the reference light. The second fluorescent reference plate 11 is disposed at a position facing the second detecting portion 5 across the conveyor path 115. Further, the second fluorescent reference plate 11 is disposed at least on an extension of a line connecting the second detecting portion 5 and the detection position B. It should be noted that the second fluorescent reference plate 11 is disposed to be separated from the detection position B by a distance L. In other words, when there is a sheet P at the detection position B, a space having the distance L exists between the sheet P and the second fluorescent reference plate 11.

The second fluorescent reference plate 11 includes, for example, glass (fluoroglass) or the like containing fluorescent material. For example, in the case where ultraviolet rays are applied to fluoroglass, the fluorescent material contained in the fluoroglass emits fluorescence. Specifically, when the excitation light is applied to the second fluorescent reference plate 11, the second fluorescent reference plate 11 emits fluorescence toward the second detecting portion 5. In other words, when there is no sheet P at the detection position B, at least part of the second fluorescent reference plate 11 appears in an image captured by the second detecting portion 5.

The shield plate 12 blocks light emitted from the lighting portion 3.

Figure 5:
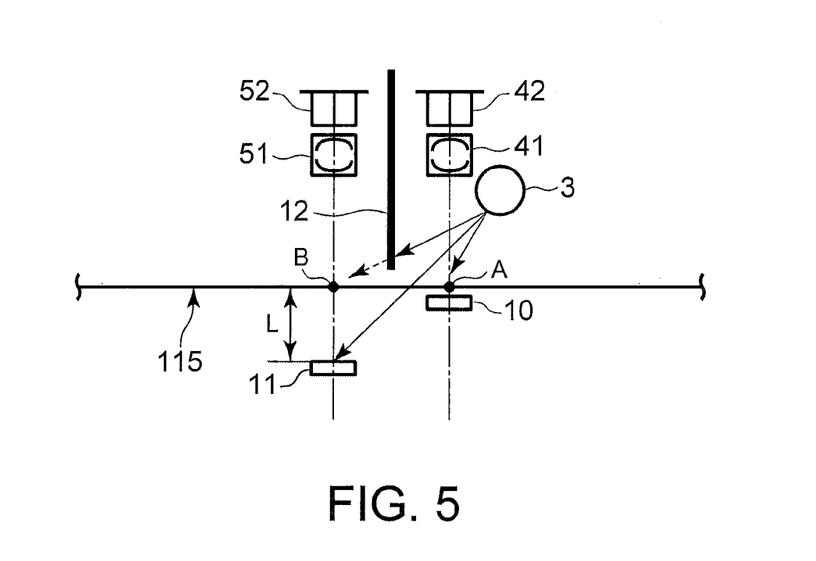
FIG. 5 is a schematic diagram showing an example of disposed positions of the portions shown in FIG. 4.

FIG. 5 is an explanatory diagram for explaining an example of the disposed position of each portion. As described previously, the first detecting portion 4 detects fluorescence. To detect fluorescence, each portion is disposed so that light emitted from the lighting portion 3 may enter at least the detection position A of the first detecting portion 4.

When there is no sheet P at the detection position A, the light emitted from the lighting portion 3 enters the first fluorescent reference plate 10 disposed in the vicinity of the detection position A. The fluorescent material contained in the first fluorescent reference plate 10 is excited by the incident light to emit light (reference light) toward the first detecting portion 4.

The second detecting portion 5 detects phosphorescence (afterglow). To detect afterglow, each portion is disposed so that the light emitted from the lighting portion 3 may not enter at least the detection position B of the second detecting portion 5. Specifically, the shield plate 12 is disposed on a line connecting the lighting portion 3 and the detection position B. The shield plate 12 blocks the light which has been emitted from the lighting portion 3 to enter the detection position B.

In the case where the second fluorescent reference plate 11 is disposed in the vicinity of the detection position B, the light emitted from the lighting portion 3 does not enter the second fluorescent reference plate 11. Accordingly, the second detecting portion 5 cannot detect the reference light emitted from the second fluorescent reference plate 11. For this reason, in this embodiment, the second fluorescent reference plate 11 is disposed to be separated from the detection position B by the distance L.

In the case where the second fluorescent reference plate 11 is disposed as shown in FIG. 5, the light emitted from the lighting portion 3 enters the second fluorescent reference plate 11 but does not enter the detection position B. As a result, the second fluorescent reference plate 11 can emit the reference light toward the second detecting portion 5, which detects phosphorescence.

The above-described arrangement enables the first detecting portion 4 to detect fluorescence from a sheet P, and enables the second detecting portion 5 to detect phosphorescence (afterglow).

In the case where each portion is disposed as shown in FIGS. 4 and 5, the second fluorescent reference plate 11 always emits fluorescence. Specifically, the second fluorescent reference plate 11 emits fluorescence even when there is a sheet P at the detection position B. Accordingly, part of the light emitted from the second fluorescent reference plate 11 is transmitted through the sheet P to enter the second detecting portion 5.

The light intensity of afterglow detected by the second detecting portion 5 has a lower value than that of fluorescence detected by the first detecting portion 4. Accordingly, in the case where afterglow is detected, the influence of transmitted light is larger compared to the case where fluorescence is detected.

In this embodiment, the second fluorescent reference plate 11 is disposed so that the second fluorescent reference plate 11, as a light source, may be separated from the conveyor path 115 by the distance (elongation distance) L. In other words, in this case, a sheet P being conveyed along the conveyor path 115 and the second fluorescent reference plate 11 are separated from each other by the elongation distance L along the optical path.

Figure 6A:
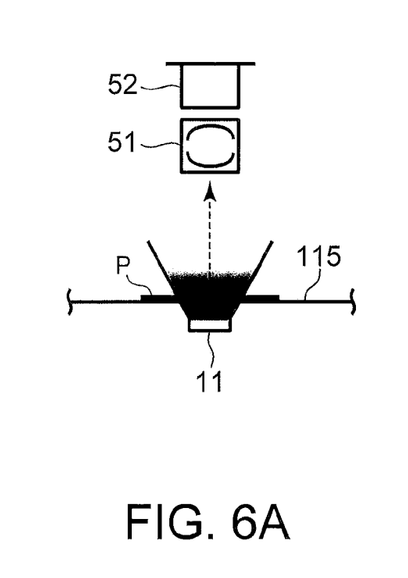
FIGS. 6A and 6B are schematic diagrams for explaining light emitted from a second fluorescent reference plate shown in FIG. 4.
Figure 6B:
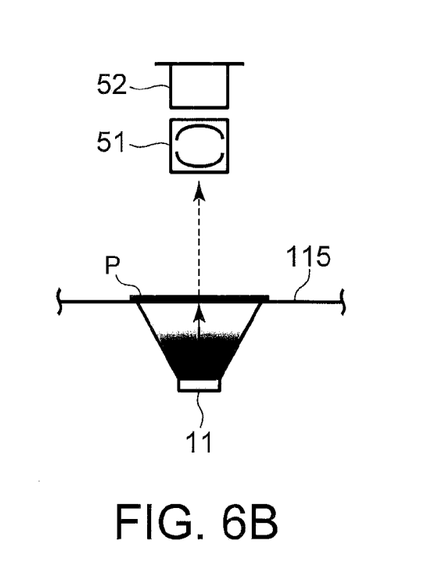

FIGS. 6A and 6B are explanatory diagrams for explaining the light emitted from the second fluorescent reference plate 11 shown in FIG. 4. FIG. 6A is a view for explaining an example in which the elongation distance L between the second fluorescent reference plate 11 and the conveyor path 115 is short. On the other hand, FIG. 6B is a view for explaining an example in which the elongation distance L between the second fluorescent reference plate 11 and the conveyor path 115 is long.

In the case where the fluorescent material of the second fluorescent reference plate 11 is excited by the light emitted from the lighting portion 3, the fluorescent material emits diffuse light. The light emitted in a diffused state enters the sheet P from the opposite side of the sheet P from the readout side to be transmitted through the sheet P. The light intensity of the light transmitted through the sheet P varies depending on the elongation distance L between the second fluorescent reference plate 11 and the sheet P. In other words, in the case where there is a sheet P at the detection position B, the intensity of the light transmitted through the detection position B on the sheet P to enter the second detecting portion 5 varies depending on the elongation distance L.

For example, in the example shown in FIG. 6A, the elongation distance L is shorter compared to the example shown in FIG. 6B. Accordingly, in the example shown in FIG. 6A, the intensity of the light transmitted through the sheet P to enter the lens 51 is higher compared to the example shown in FIG. 6B.

Figure 7A:
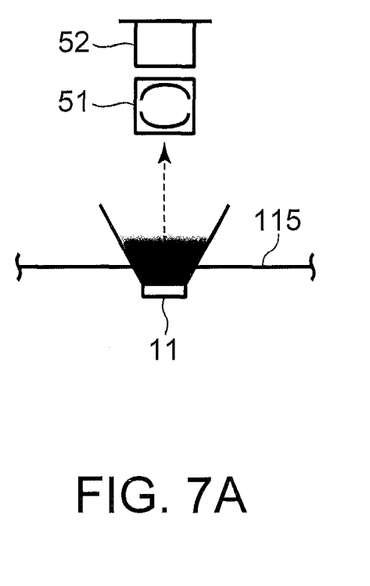
FIGS. 7A and 7B are schematic diagrams for explaining light emitted from a second fluorescent reference plate shown in FIG. 4.
Figure 7B:
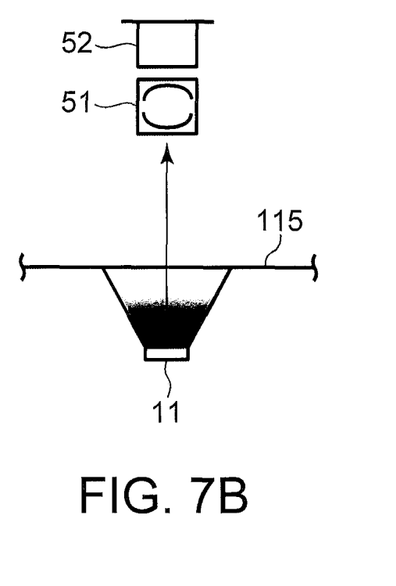

FIGS. 7A and 7B are explanatory diagrams for explaining the light emitted from the second fluorescent reference plate 11 shown in FIG. 4. FIG. 7A is a view for explaining an example in which the elongation distance L between the second fluorescent reference plate 11 and the conveyor path 115 is short. On the other hand, FIG. 7B is a view for explaining an example in which the elongation distance L between the second fluorescent reference plate 11 and the conveyor path 115 is long.

When there is no sheet P at the detection position B, the light emitted from the second fluorescent reference plate 11 directly enters the second detecting portion 5. In this case, since the light is not transmitted through the sheet P, the light intensity is not attenuated. As a result, the second detecting portion 5 can detect light at almost equal levels in both the examples shown in FIGS. 7A and 7B.

In other words, when light is detected by the second detecting portion 5 in the state in which there is no sheet P at the detection position B, the second detecting portion 5 detects the second fluorescent reference plate 11 itself. Accordingly, the light intensity of the light detected by the second detecting portion 5 does not vary at least within the range of the focal depth of the second detecting portion 5.

The light intensity of the light transmitted through a sheet P is also influenced by the width of the second fluorescent reference plate 11. The quantity of the fluorescent material contained in the entire second fluorescent reference plate 11 varies depending on the width of the second fluorescent reference plate 11 with respect to the conveying direction of the sheet P.

For example, in the case where the width of the second fluorescent reference plate 11 is large, the total quantity of fluorescence emitted from the entire second fluorescent reference plate 11 is large. In the case where the width of the second fluorescent reference plate 11 is small, the total quantity of fluorescence emitted from the entire second fluorescent reference plate 11 is small. In other words, reducing the width of the second fluorescent reference plate 11 can reduce the light transmitted through a sheet P.

Figure 8:
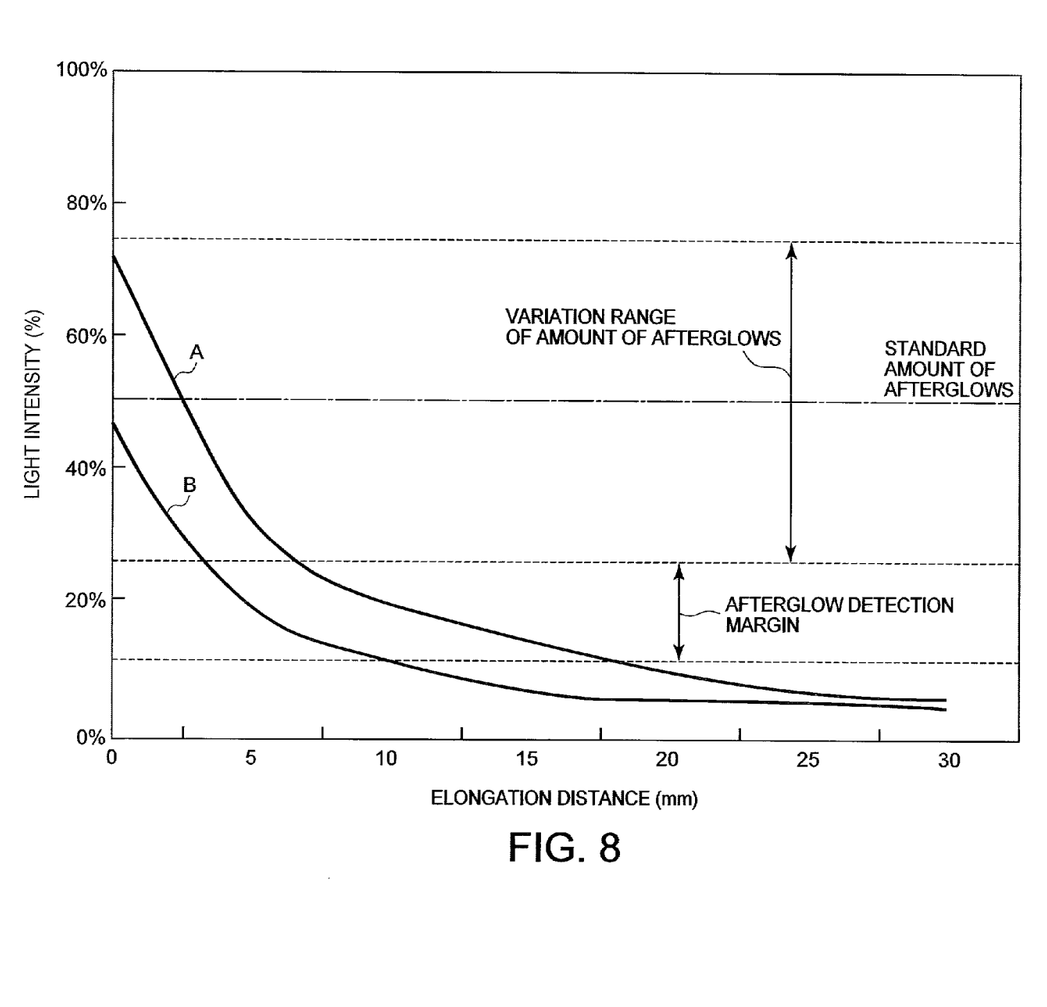
FIG. 8 is a graph for explaining the relationship between light transmitted through a sheet and an elongation distance.

FIG. 8 is a graph for explaining the relationship between the light transmitted through a sheet P and the elongation distance L. FIG. 8 shows an example in which the intensity of the reference light detected from the second fluorescent reference plate 11 by the second detecting portion 5 in a state where there is no sheet P at the detection position B is set as 100%.

Graph A shows an example in which the width of the second fluorescent reference plate 11 with respect to the conveying direction is 10 mm. On the other hand, graph B shows an example in which the width of the second fluorescent reference plate 11 with respect to the conveying direction is 5 mm.

The state of the phosphorescent printed information printed on a sheet P varies due to soiling, aging, or the like. For example, a change in the quantity of the phosphorescent material applied as phosphorescent information causes a change in the light intensity of afterglow emitted from the phosphorescent material.

A standard value of the light intensity of the afterglow is assumed to be 50% of the intensity of the reference light, and the variation range of the light intensity of the afterglow is assumed to be 50% of the intensity of the reference light. In this case, the second detecting portion 5 detects the afterglow as light having an intensity of 25% to 75% of the intensity of the reference light.

Based on the above-described assumptions, if the light intensity of the light transmitted through a sheet P is less than approximately 10% of the intensity of the reference light, the afterglow can be detected with high accuracy. It should be noted that the range of 25% to 10% of the intensity of the reference light is assumed to be a margin for detecting the afterglow with high accuracy.

As shown in FIG. 8, in the case where the width of the second fluorescent reference plate 11 with respect to the conveying direction is 10 mm, if the elongation distance L is approximately 20 mm, the light intensity of the light transmitted through a sheet P can be reduced to less than 10% of the intensity of the reference light. On the other hand, in the case where the width of the second fluorescent reference plate 11 with respect to the conveying direction is 5 mm, if the elongation distance L is approximately 10 mm, the light intensity of the light transmitted through a sheet P can be reduced to less than 10% of the intensity of the reference light.

As described above, the light detection device 135 of this embodiment includes, on the side of the second detecting portion 5 for detecting the afterglow, the second fluorescent reference plate 11 disposed to be separated from the conveyor path 115 by the elongation distance L. The elongation distance L is set so that the light from the lighting portion 3 on the first detecting portion 4 side may enter the second fluorescent reference plate 11 and that the light emitted from the second fluorescent reference plate 11 may not influence the result of detection of the afterglow by the second detecting portion 5.

Thus, the reference light can be supplied to the second detecting portion 5. Also, in the case where the afterglow is detected, the transmitted light can be prevented from influencing the result of detection. As a result, it is possible to provide a light detection device in which correction can be performed on a fluorescence detecting portion and a phosphorescence detecting portion, and a sheet processing apparatus including the light detection device.

It should be noted that though the above-described embodiment has been described with the width of the second fluorescent reference plate 11 with respect to the conveying direction being assumed to be 5 mm or 10 mm, the present invention is not limited to this configuration. The second fluorescent reference plate 11 may have any width as long as the width is at least not less than the scanning width of the second detecting portion 5.

The elongation distance L between the conveyor path 115 and the second fluorescent reference plate 11 may be any distance as long as the reference light does not influence the result of detection by the second detecting portion 5. For example, the light intensity of the reference light emitted from the second fluorescent reference plate 11 differs depending on the material and the like of the fluorescent material contained in the second fluorescent reference plate 11. In other words, the elongation distance L needs to be appropriately set in accordance with the light intensity of the reference light emitted from the second fluorescent reference plate 11.

Figure 9:
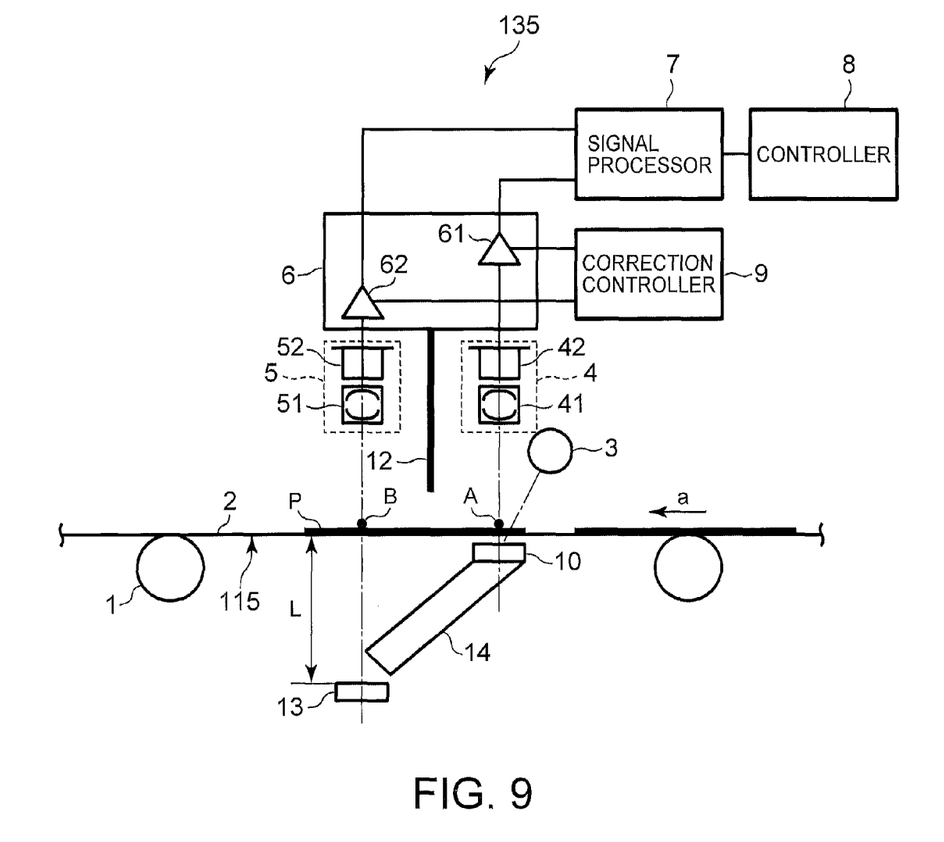
FIG. 9 is a simplified diagram for schematically showing the configuration of a light detection device according to a second embodiment.

Next, a second embodiment will be described. FIG. 9 is an explanatory diagram for explaining an example of the configuration of a light detection device 135 according to the second embodiment. It should be noted that components similar to those in the first embodiment are denoted by the same reference signs and will not be further described in detail.

The light detection device 135 shown in FIG. 9 includes a lighting portion 3, first and second detecting portions 4 and 5, an amp circuit 6, a signal processor 7, a controller 8, a correction controller 9, a fluorescent reference plate 10, a shield plate 12, a reflection white plate 13, and a light guide plate 14.

The reflection white plate 13 is a reflecting diffuser which diffuses and reflects incident light. The reflection white plate 13 is disposed to be separated from a conveyor path 115 by an elongation distance L. In other words, the reflection white plate 13 is disposed to be separated from a detection position B on the conveyor path 115 by the elongation distance L along the optical path. The light guide plate 14 is a light guide which guides incident light. The light guide plate 14 is disposed to face a lower portion of the fluorescent reference plate 10. The light guide plate 14 receives reference light emitted from the fluorescent reference plate 10, and guides the received reference light so that the received reference light may enter the reflection white plate 13.

The lighting portion 3 applies light to the fluorescent reference plate 10. The fluorescent reference plate 10 is excited by the light to emit fluorescence as reference light. The light guide plate 14 guides the fluorescence emitted from the fluorescent reference plate 10 inside. The light guide plate 14 emits the light guided inside toward the reflection white plate 13. The reflection white plate 13 diffuses and reflects the incident fluorescence. The fluorescence diffused and reflected by the reflection white plate 13 enters the second detecting portion 5. In this case, the reflection white plate 13 functions as a reference member for supplying the second detecting portion 5 with the reference light.

In the above-described configuration, in the case where there is no sheet P at the detection position B, the fluorescence emitted from the fluorescent reference plate 10 is reflected by the reflection white plate 13 to enter the second detecting portion 5. In other words, the second detecting portion 5 can acquire the reference light as a detection reference. As a result, the correction controller 9 can control the gain of an amplifier 62. Also, since the conveyor path 115 and the reflection white plate 13 are disposed to be separated from each other by the elongation distance L, it is possible to reduce the influence of the light emitted from the reflection white plate 13 on a result of detection by the second detecting portion 5.

Figure 10:
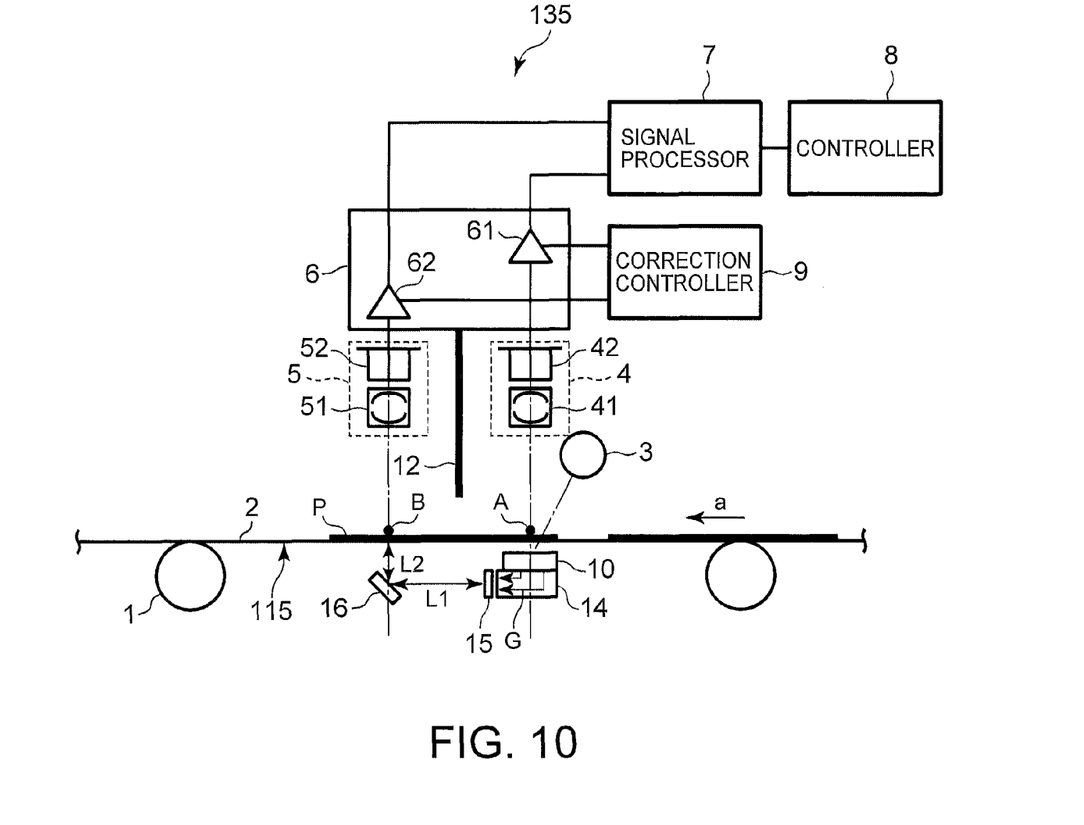
FIG. 10 is a simplified diagram for schematically showing the configuration of a light detection device according to a third embodiment.

Next, a third embodiment will be described. FIG. 10 is an explanatory diagram for explaining an example of the configuration of a light detection device 135 according to the third embodiment. It should be noted that components similar to those in the first and second embodiments are denoted by the same reference signs and will not be further described in detail.

The light detection device 135 shown in FIG. 10 includes a lighting portion 3, first and second detecting portions 4 and 5, an amp circuit 6, a signal processor 7, a controller 8, a correction controller 9, a fluorescent reference plate 10, a shield plate 12, a light guide plate 14, a transparence white plate 15, and a reflection mirror 16.

The transparence white plate 15 is a translucent reflector which diffuses and transmits incident light. The transparence white plate 15 is disposed at an output end of the light guide plate 14. The light guide plate 14 receives reference light emitted from the fluorescent reference plate 10, and guides the received reference light so that the received reference light may enter the transparence white plate 15. The reflection mirror 16 is a reflector which reflects light. The reflection mirror 16 is disposed at such a position that the reflection mirror 16 can cause light emitted from the transparence white plate 15 to enter the second detecting portion 5.

The lighting portion 3 applies light to the fluorescent reference plate 10. The fluorescent reference plate 10 is excited by the light to emit fluorescence as reference light. The light guide plate 14 guides the fluorescence emitted from the fluorescent reference plate 10 inside. The light guide plate 14 guides the light guided inside in the direction indicated by arrows G shown in FIG. 10, and emits the light from the output end. The transparence white plate 15 diffuses the light emitted from the output end of the light guide plate 14. The reflection mirror 16 reflects the light diffused by the transparence white plate 15 and causes the light to enter the second detecting portion 5. In this case, the transparence white plate 15 functions as a reference member for supplying the second detecting portion 5 with the reference light.

It should be noted that the reflection mirror 16 is disposed to be separated from the transparence white plate 15 by a distance L1. Further, the reflection mirror 16 is disposed to be separated from the conveyor path 115 by a distance L2. In this case, the sum of the distances L1 and L2 corresponds to the elongation distance L of the first embodiment. Specifically, in this configuration, the transparence white plate 15 as a reference member and a detection position B on the conveyor path 115 are separated from each other by the sum of the distances L1 and L2 along the optical path.

In the above-described configuration, in the case where there is no sheet P at the detection position B, the fluorescence emitted from the fluorescent reference plate 10 is reflected by the reflection mirror 16 to enter the second detecting portion 5. In other words, the second detecting portion 5 can acquire the reference light as a detection reference. As a result, the correction controller 9 can control the gain of an amplifier 62. Also, the length of the optical path from the transparence white plate 15 to the conveyor path 115 is L1+L2. Setting the distances L1 and L2 at not less than predetermined lengths makes it possible to reduce the influence of the light emitted from the transparence white plate 15 on the result of detection by the second detecting portion 5.

This invention is not limited to the above-described embodiments themselves, but, in a practical phase, can be realized by modifying components without departing from the spirit of the invention. Moreover, various inventions can be formed using appropriate combinations of some of the components disclosed in each of the above-described embodiments. For example, in any of the embodiments, some of all the components described therein may be deleted. Furthermore, components of different embodiments may be appropriately combined.

What is claimed is:

1. A light detection device comprising:
   a first sensor which detects fluorescence from a first detection position on a conveyor path along which a sheet is conveyed;
   a second sensor which detects afterglow from a second detection position on the conveyor path along which the sheet is conveyed;
   a lighting device which applies excitation light over a range including the first detection position and not including the second detection position;
   a first reference plate which emits reference light toward the first sensor, the first reference plate including fluorescent material which emits fluorescence by being excited by the lighting device;
   a second reference plate which emits reference light toward the second sensor when the sheet is present at the second detection position, the reference light not influencing a result of detection by the second sensor; and
   a correction controller which corrects a result of detection by the first sensor based on the reference light emitted by the first reference plate and detected by the first sensor and to correct a result of detection by the second sensor based on the reference light emitted by the second reference plate and detected by the second sensor.

2. The light detection device according to claim 1, wherein the second reference plate is disposed to be separated from the second detection position by a predetermined distance along an optical path, and emits diffuse reference light.

3. The light detection device according to claim 2, wherein the second reference plate includes fluorescent material which emits fluorescence by being excited by the lighting device, and is disposed at a position which the light emitted from the lighting device enters.

4. The light detection device according to claim 2, further comprising:
   a light guide plate which receives the reference light emitted from the first reference plate, and to guide the received reference light so that the received reference light enters the second reference plate, wherein
   the second reference plate diffusely reflects the reference light entering through the light guide plate.

5. The light detection device according to claim 2, further comprising:
   a light guide plate which receives the reference light emitted from the first reference plate, and to guide the received reference light so that the received reference light enters the second reference plate; and
   a reflection mirror which reflects incident light, wherein
   the second reference plate diffusely transmits the reference light entering through the light guide plate, and the reflection mirror reflects the reference light diffused by the second reference plate and causes the reference light diffused by second reference plate to enter the second sensor.

6. The light detection device according to claim 2, wherein the predetermined distance is set based on a detected transmittance of the sheet and a detected intensity of light emitted by the second reference plate.

7. A sheet processing apparatus comprising:
   a conveyor path which conveys a sheet;
   a first sensor which detects fluorescence from a first detection position on the conveyor path along which the sheet is conveyed;
   a second sensor which detects afterglow from a second detection position on the conveyor path along which the sheet is conveyed;
   a lighting device which applies excitation light over a range including the first detection position and not including the second detection position;
   a first reference plate which emits reference light toward the first sensor, the first reference plate including fluorescent material which emits fluorescence by being excited by the lighting device;
   a second reference plate which emits reference light toward the second sensor when the sheet is present at the second detection position, the reference light not influencing a result of detection by the second sensor; and
   a correction controller which corrects a result of detection by the first sensor based on the reference light emitted by the first reference plate and detected by the first sensor and to correct a result of detection by the second sensor based on the reference light emitted by the second reference plate and detected by the second sensor;
   a determination controller which determines whether or not the sheet contains each of fluorescent printed information and phosphorescent printed information, based on a fluorescent image detected by the first sensor and an afterglow image detected by the second sensor; and
   a classification processor which determines a type of the sheet based on a result of the determination by the determination portion and classifies the sheet by type.

8. The sheet processing apparatus according to claim 7, wherein the second reference plate is disposed to be separated from the second detection position by a predetermined distance along an optical path, and emits diffuse reference light.

9. The sheet processing apparatus according to claim 8, wherein the second reference plate includes fluorescent material which emits fluorescence by being excited by the lighting device, and is disposed at a position which the light emitted from the lighting device enters.

10. The sheet processing apparatus according to claim 8, further comprising:
    a light guide plate which receives the reference light emitted from the first reference plate, and to guide the received reference light so that the received reference light enters the second reference plate, wherein
    the second reference plate diffusely reflects the reference light entering through the light guide plate.

11. The sheet processing apparatus according to claim 8, further comprising:
    a light guide plate which receives the reference light emitted from the first reference plate, and to guide the received reference light so that the received reference light enters the second reference plate; and
    a reflection mirror which reflects incident light, wherein
    the second reference plate diffusely transmits the reference light entering through the light guide plate, and the reflection mirror reflects the reference light diffused by the second reference plate and causes the reference light diffused by the second reference plate to enter the second sensor.

12. The sheet processing apparatus according to claim 8, wherein the predetermined distance is set based on a detected transmittance of the sheet and a detected intensity of light emitted by the second reference plate.

* * * * *